United States Patent [19]

Scotese et al.

[11] 4,324,893

[45] Apr. 13, 1982

[54] 4-AMINO-3-CARBOXY OR CYANO-1,2-DIHYDRO-2-OXO-1,8-NAPHTHYRIDINE DERIVATIVES

[75] Inventors: Anthony C. Scotese, King of Prussia; Arthur A. Santilli, Havertown, both of Pa.

[73] Assignee: American Home Products Corporation, New York, N.Y.

[21] Appl. No.: 125,600

[22] Filed: Feb. 28, 1980

Related U.S. Application Data

[63] Continuation-in-part of Ser. No. 31,255, Apr. 18, 1979, abandoned.

[51] Int. Cl.$^3$ .............................................. C07D 413/04
[52] U.S. Cl. .................................. 544/127; 544/58.6; 544/362; 546/123
[58] Field of Search ...................... 544/58.6, 127, 362; 546/123

[56] References Cited

U.S. PATENT DOCUMENTS

3,849,421 11/1974 Nakagome et al. ................. 546/122
3,993,656 11/1976 Rooney et al. ...................... 546/122
4,103,257 7/1978 Hammond et al. ................. 546/123
4,133,885 1/1979 Bolhefer et al. .................... 424/256

FOREIGN PATENT DOCUMENTS

1397869 6/1975 United Kingdom.

OTHER PUBLICATIONS

Williams et al., *Chem. Abstracts*, vol. 80, No. 37087m, (1979).
Seide, *Chem. Ber.*, vol. 59, (1926), pp. 2465–2473.
Petrow et al., *J. Chem. Soc.*, (1947), pp. 1407–1410.
Mangini et al., *Gazz. Chimica Ital.*, vol. 72, (1942), pp. 183–197.
Carboni et al., *Farmaco Ed. Sci.*, vol. 28, (1973), pp. 722–732.
Tonetti et al., *Farmaco Ed. Sci.*, vol. 31, (1976), pp. 175–182.

*Primary Examiner*—Henry R. Jiles
*Assistant Examiner*—R. W. Ramsuer
*Attorney, Agent, or Firm*—Richard K. Jackson

[57] ABSTRACT

4-Amino-3-carboxy or cyano-1,2-dihydro-2-oxo-1,8-naphthyridine derivatives are anti-secretory agents for use in the treatment of peptic ulcer disease.

42 Claims, No Drawings

4-AMINO-3-CARBOXY OR CYANO-1,2-DIHYDRO-2-OXO-1,8-NAPHTHYRIDINE DERIVATIVES

CROSS-REFERENCE TO CO-PENDING APPLICATION

This application is a continuation-in-part of co-pending Application Ser. No. 31,255, filed Apr. 18, 1979, abandoned.

BRIEF DESCRIPTION OF THE INVENTION

In accordance with this invention there is provided a group of substituted 4-amino-3-carboxy or cyano-1,2-dihydro-2-oxo-1,8-naphthyridine derivatives which act as gastric anti-secretory agents and are useful in the treatment of peptic ulcer disease. In addition, the 4-halo-3-trichloromethyl, carboxy or cyano-1,2-dihydro-2-oxo-1,8-naphthyridine intermediate precursors useful in production of the anti-secretory agents, provided another aspect of the invention.

The anti-ulcer agents of this invention function in their anti-secretory capacity to reduce (1) total gastric volume, (2) hydrogen ion secretion, or (3) hydrogen ion concentration. The reduction of any one of these parameters aids in attenuating the general debilitating influence of a peptic ulcer. The use of compounds exhibiting anti-secretory activity in the curative and/or prophylactic treatment of peptic ulcer disease is an established, beneficial procedure.

DETAILED DESCRIPTION OF THE INVENTION

The anti-secretory agents of this invention are compounds of the formula:

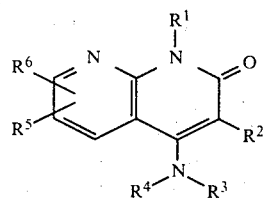

in which $R^1$ is hydrogen, alkyl of 1 to 6 carbon atoms, cycloalkyl of 5 to 6 carbon atoms, alken-(3, 4, 5 or 6)-yl of 3 to 6 carbon atoms or alkyn-(3, 4, 5 or 6)-yl of 3 to 6 carbon atoms;

$R^2$ is —CN, —CO$_2$H, —CO$_2$R$^7$ where $R^7$ is alkyl of 1 to 6 carbon atoms, —CONHNH$_2$ or

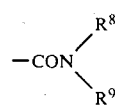

where $R^8$ and $R^9$ are independently hydrogen or alkyl of 1 to 6 carbon atoms;

$R^3$ and $R^4$ are, independently, hydrogen, alkyl of 1 to 6 carbon atoms, hydroxyalkyl of 1 to 6 carbon atoms, dialkylaminoalkyl of 4 to 8 carbon atoms, alkanoyl of 2 to 4 carbon atoms, haloalkanoyl of 2 to 4 carbon atoms, or when taken together with the nitrogen atom to which they are attached, $R^3$ and $R^4$ complete a heterocyclic group selected from aziridinyl, azetidinyl, pyrrolidinyl, piperidinyl, piperazinyl, 4-lower alkylpiperazinyl, 4-phenyl-piperazinyl, 4-[1-ethyl-1,2-dihydro-7-methyl-2-oxo-1,8-naphthyridine-4-yl-3-carboxylic acid ethyl ester]-piperazinyl, 4-carb-(lower)alkoxypiperazinyl, morpholinyl, thiomorpholinyl or a ring substituted lower alkyl analogue thereof;

$R^5$ and $R^6$ are independently hydrogen, alkyl of 1 to 4 carbon atoms, halo, alkylamino of 1 to 4 carbon atoms, or alkoxy of 1 to 6 carbon atoms;

or a pharmaceutically acceptable salt thereof.

The preferred compounds of the group described in the preceding paragraph from the standpoint of potency as anti-secretory agents are those of the formula:

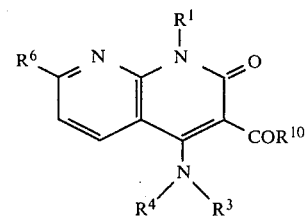

in which $R^1$ is hydrogen, methyl, ethyl, propyl, allyl, propargyl, cyclohexyl, or isobutyl;

$R^3$ is hydrogen, alkyl of 1 to 6 carbon atoms or trifluoroacetyl;

$R^4$ is hydrogen, alkyl of 1 to 6 carbon atoms, or when taken with $R^3$ and the nitrogen atom to which they are attached forms a heterocyclic group selected from pyrrolidinyl, morpholinyl, piperazinyl, or 4-methylpiperazinyl;

$R^6$ is hydrogen or methyl;

and $R^{10}$ is hydroxy, alkoxy of 1 to 6 carbon atoms or hydrazinyl;

or a pharmaceutically acceptable salt thereof.

Those compounds containing a basic amino group is the 4-position, such as the piperazinyl and dialkylaminoalkyl groups, are capable of forming acid addition salts. It is intended throughout this specification and claims to embrace the pharmaceutically acceptable salts of such compounds, which salts are conveniently derived from such acids as hydrochloric, hydrobromic, sulfuric, phosphoric, methane sulfonic, nitric, p-toluene sulfonic, acetic, citric, maleic, succinic acid and the like. In addition, the the compounds in their free carboxylic acid form are converted by standard techniques well-known to the chemist into alkali metal (sodium or potassium), alkaline earth metal (calcium or magnesium), ammonium or primary, secondary and tertiary alkylamine salts, the latter containing from 1 to 6 carbon atoms in their alkyl moieties. The expressions lower alkyl and lower alkoxy are intended to embrace groups containing from 1 to 6 carbon atoms and preferably 1 to 4 carbon atoms. The term halo means chloro, bromo, iodo, or fluoro, preferably chloro or bromo.

Each of the anti-secretory agents disclosed herein was found active in the following scientifically recognized, standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally. The rats are sacrificed by $CO_2$ asphyxiation four hours after pyloric ligtion. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometic titration to pH 7.0 with 0.1 N NaOH. The calculated product of gastric volume (ml/4 hr.) and acid concentration (mEq/L) estimates the total acid output (TAO, mEq/4 hr.) over the four-hour test period. An anaysis of variance is performed on these data to determine statistically significant ($p<0.05$) derivation between control versus drug-treated groups.

In addition to anti-secretory activity, certain compounds of this invention possess diuretic activity and they are useful for treatment of conditions requiring diuresis therapy. The diuretic agents disclosed herein are those compounds in which the substituent in 4 position is primary amino. Thus, the compounds possessing diuretic activity may be depicted by the structural formula:

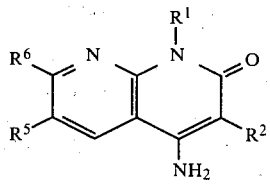

in which each of the R groups is defined in conjunction with the structural formula generically depicting compounds with anti-secretory activity. The 4-amino-1,8-naphthyridine derivatives demonstrated effectiveness generally comparable to hydrochlorothiazide in the standard, scientifically recognized test procedure of Lipschitz et al., J. Pharmacol. Exp. Therap., 79, 97 (1945) wherein male Sprague-Dawley rats 14 to 17 weeks old (175–200 grams), after fasting for one day are given an oral physiological saline prime dose of 25 ml/kg. containing 25 mg/kg. of the compound being tested. Each compound is given to 8 rats, urea at a dose of 960 mg/kg. is given as a standard of comparison to 8 rats and saline alone is given to 8 more rats as a control. The animals are placed in metabolism cages, 2 rats per cage, and urine is collected for 3 hours. Volume of urine, sodium and potassium are determined and compared to the control to obtain the ratio of activity.

The dosage regimen for therapeutic use of the anti-secretory agents disclosed herein will vary with the mode of administration, size and age of the person under treatment as well as the severity of the dysfunction. Therefore, treatment of peptic ulcer disease must be individualized for the patient under the guidance of the attending physician. The use of the 4-amino-1,8-naphthyridines as diuretics must similarly be controlled in the human. Where two conditions occur simultaneously in the same patient, requiring treatment of peptic ulcer disease as well as diuresis, the 4-amino-1,8-naphthyridines afford the decided advantages of single compound treatment for both problems. Where the conditions occur separately, the second activity of the 4-amino-1,8-naphthyridines is not deleterious and not contraindicative of applicability of the treatment.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of providing suitable pharmaceutically acceptable solid or liquid dosage units.

The intermediate 4-halo-naphthyridine precursors for production of the anti-secretory agents of this invention are compounds of the formula:

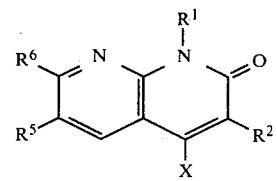

in which $R^1$ is hydrogen, alkyl of 1 to 6 carbon atoms, cycloalkyl of 5 to 6 carbon atoms, alken-(3, 4, 5 or 6)-yl of 3 to 6 carbon atoms, or alkyn-(3, 4, 5 or 6)-yl of 3 to 6 carbon atoms;

$R^2$ is $-CCl_3$, $-CN$, $-CO_2H$, or $-CO_2R^7$ where $R^7$ is alkyl of 1 to 6 carbon atoms;

X is chloro, bromo, or iodo;

and $R^5$ and $R^6$ are, independently, hydrogen, halo, alkoxy of 1 to 6 carbon atoms, alkylamino of 1 to 4 carbon atoms, or alkyl of 1 to 4 carbon atoms.

The preferred intermediates are those conforming in structure to the preferred group of anti-secretory agents.

The 4-substituted amino-3-carboxy or cyano-1,2-dihydro-2-oxo-1,8-naphthyridine derivatives of this invention are prepared by Process 1 which involves reacting a primary or secondary amine with an appropriately substituted 4-halo-naphthyridine precursor. By 4-halo, applicants intend to embrace the chloro, bromo and iodo derivatives. The 4-halo-naphthyridine precursors are prepared by conventional techniques involving displacement of a 4-hydroxyl group from the corresponding 4-hydroxy-naphthyridine with such halogenating reagents as thionyl chloride to obtain the 4-chloro-naphthyridines and phosphorus oxybromide to obtain the 4-bromo-naphthyridines. The 4-iodo-naphthyridines are prepared by reaction of a 4-chloro-naphthyridine with sodium iodide in an appropriate inert solvent such as acetone.

Alternatively, the 4-chloro, bromo or iodo-naphthyridines may also be prepared directly by nitrosation of the appropriately ring substituted 4-amino-naphthyridines in hydrochloric, hydrobromic or hydroidic acid, respectively.

The 4-amino-3-carboxy-1,2-dihydro-2-oxo-1,8-naphthyridine derivatives of this invention are prepared directly from a 2-subsituted amino nicotinonitrile reacting with a lower alkyl malonyl chloride followed by a Dieckman ring closure with sodium alkoxide, or an analogous strong base such as potassium alkoxide or NaH or $NaNH_2$ in a aprotic solvent, thusly:

Process 2

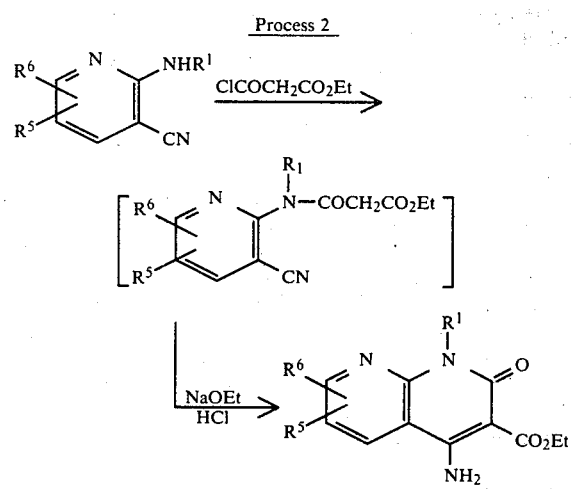

Alternatively, the 2-substituted aminonicotinonitrile may be reacted with the sodio salt of a di-lower alkyl malonate to give directly on acidification the 4-amino-3-carboxy-1,2-dihydro-2-oxo-1,8-naphthyridine derivative, thusly:

Process 3

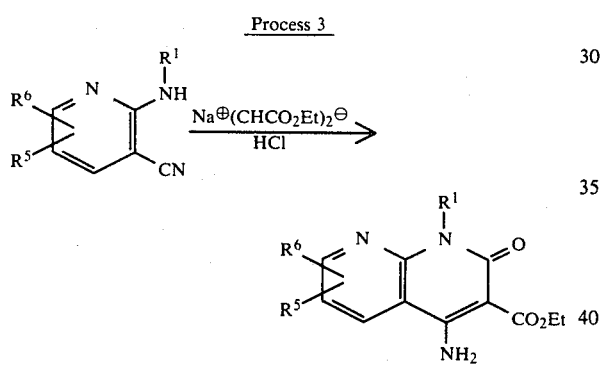

where $R^1$ in the preceding equation is hydrogen, the product may be treated with a lower alkali metal alkoxide and alkylated with a lower alkyl, alkenyl or alkynyl iodide, bromide, or chloride (RX where R contains 1 to 6 carbon atoms) to afford alternatively the 1-alkyl-, alkenyl- or alkynyl-4-amino-3-carboxy-1,2-dihydro-2-oxo-1,8-naphthyridine derivatives described above.

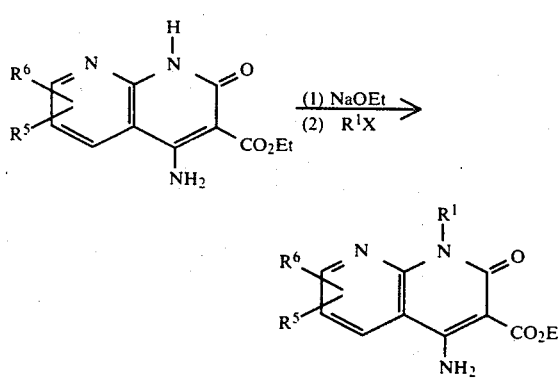

The amide substituent

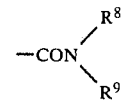

representing $R^2$ is readily produced at 3-position of the 4-amino and 4-substituted amino-3-alkoxycarbonyl-1,8-naphthyridine derivatives by reaction of the ester —$CO_2R^7$ with ammonia or a primary or secondary alkylamine by conventional techniques in which the alkyl group(s) independently contain from 1 to 6 carbon atoms.

The 4-amino-3-carboxy or cyano-1,2-dihydro-2-oxo-1,8-naphthyridine derivatives may also be prepared by reaction of ammonia with an appropriately substituted 3-trichloromethyl-4-chloro-1,8-naphthyridine derivative, thusly:

Process 4

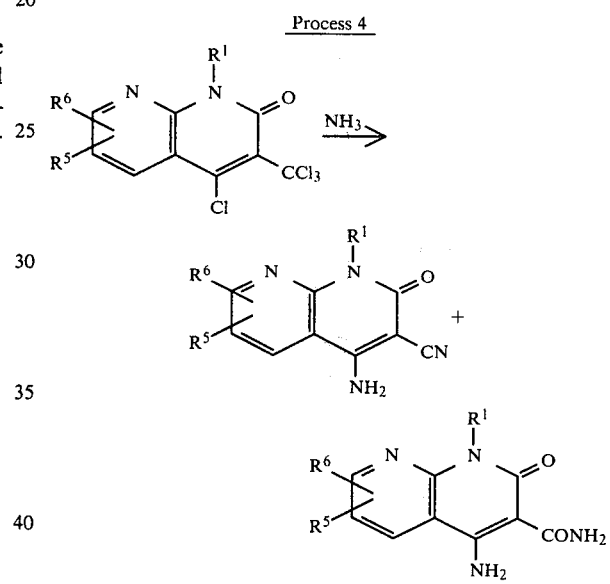

The 3-trichloromethyl-4-chloro-1,8-naphthyridine precursor is obtained by reaction of the corresponding 3-carboethoxy-4-hydroxynaphthyridine with $PCl_5$, thusly:

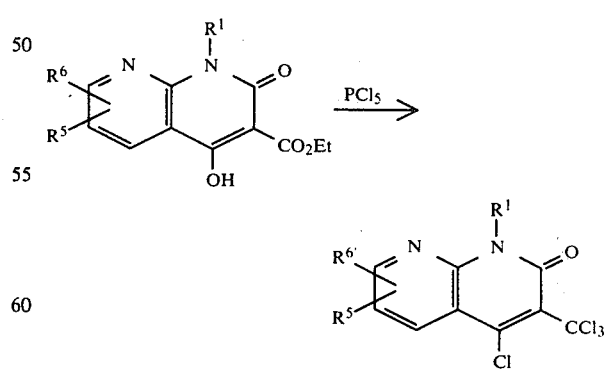

The following examples illustrate the preparation of representative intermediates and final products of the invention. An index of drug gastric anti-secretory activity is reported at the end of each example illustrating its production. These data, expressed as percentage inhibition, shown the reduction of acid secretion in drug-treated compared to control groups based upon i.d. administration of 32 mg/kg. of the tested compound.

EXAMPLE 1

4-Amino-1,2-Dihydro-2-Oxo-1,8-Naphthyridine-3-Carboxylic Acid Ethyl Ester

To a solution of 4.14 g. (0.18 g. atom) of sodium in 100 ml. of ethanol was added 28.8 g. (0.18 mole) of diethyl malonate. After stirring at room temperature for 5 minutes, 7.14 g. (0.06 mole) of 2-aminonicotinonitrile was added and the mixture was heated under reflux for 6 hours. The mixture was cooled and was diluted with 100 ml. of water and was acidified with conc. hydrochloric acid. On cooling, a precipitate was formed which was collected and was triturated with 1000 ml. of boiling ethanol. The mixture was filtered and the filtrate was cooled in ice to precipitate 2.9 g. of product, m.p. 264°-267° C. dec.

Analysis for: $C_{11}H_{11}N_3O_5$; Calculated: C, 56.65; H, 4.75; N, 18.02; Found: C, 56,37; H, 4.79; N, 18.08; Percentage Inhibition: 68%.

EXAMPLE 2

4-Amino-1,2-Dihydro-2-Oxo-1,8-Naphthyridine-3-Carboxylic Acid

The material which was insoluble in boiling ethanol from the previous reaction was recrystallized from N,N-dimethylformamide to give a small amount of the corresponding carboxylic acid, m.p. 296°-298° C. dec.

Analysis for: $C_9H_7N_3O_3$; Calculated: C, 52.68; H, 3.44; N, 20.48; Found: C, 52.27; H, 3.72; N, 20.23.

EXAMPLE 3

4-Chloro-1,2-Dihydro-1-Methyl-2-Oxo-1,8-Naphthyridine-3-Carboxylic Acid, Ethy Ester To 200 ml. of anhydrous N,N-dimethylformamide was added 1.9 g. (0.04 mole) of 50% sodium hydride. Then 6.5 g. (0.04 mole) of 3,4-dihydro-1,3-dioxo-1H-pyrido[2,3-d][1,3]oxazine was added in portions over 5 minutes. After 14.2 g. (0.1 mole) of methyl iodide was added, the mixture was stirred at room temperature for 2 hours. The mixture was cooled and water was slowly added. On further dilution of water, a precipitate was formed which was collected, air dried and was recrystalized from ethanol to give 2.6 g. of 1-methyl-1H-4H-pyrido[2,3-d][1,3]oxazine-2,4-dione, m.p. 163°-166° C.

Analysis for $C_8H_6N_2O_3$; Calculated: C, 53.93; H, 3,40; N, 15.73; Found: C, 53.60; H, 3.52; N, 15.87.

To a solution of 0.345 g. (0.15 g. atom) of sodium in 30 ml. of ethanol was added 4.8 g. of diethyl malonate. The mixture was stirred at room temperature for 5 minutes and then evaporated in a rotary evaporator. The residue was dissolved in 30 ml. of N,N-dimethylformamide and 2.67 g. (0.015 mole) of 1-methyl-1H-4H-pyrido[2,3-d][1,3]-oxazine-2,4-dione was added. The mixture was heated under reflux for 10 minutes and the thick mixture was dissolved in 100 ml. of water. The solution was acidified with conc. hydrochloric acid and the precipitate which formed was collected, air dried, and a small amount of this 1.7 g. was recrystallized from ethanol to give the analytical sample of 4-hydroxy-1,2-dihydro-1-methyl-2-oxo-1,8-naphthyridine-3-carboxylic acid, ethyl ester, m.p. 158°-160° C.

Analysis for: $C_{12}H_{12}N_2O_4$; Calculated: C, 58.06; H, 4.87; N, 11.29; Found: C, 57.86; H, 4.85; N, 11.18.

A stirred mixture of 1.7 g. of 4-hydroxy-1,2-dihydro-1-methyl-2-oxo-1,8-naphthyridine-3-carboxylic acid ethyl ester in 25 ml. of phosphorus oxychloride was heated under reflux for 2 hours. The phosphorus oxychloride was removed in a rotary evaporator and the residue was poured into 100 ml. of ice water. The precipitate which formed was collected, air dried and a small amount of the 1.9 g. was recrystallized from heptane twice to give the analytical sample of the title compound, m.p. 132°-135° C.

Analysis for: $C_{12}H_{11}ClN_2O_3$; Calculated: C, 54.04; H, 4.16; N, 10.51; Found: C, 53.61; H, 4.16; N, 10.51.

The corresponding intermediate in which $R^5$ and $R^6$ are independently alkyl of 1 to 4 carbon atoms are prepared in the same manner, employing the appropriate alkyl substituted precursor. By analogous procedures, the intermediates for amine introduction in 4-position useful in the preparation of the variously substituted compounds of this invention are readily obtained. Likewise, the initial pyrido-oxazine reactant may be alkylated with alkyl iodides of 1 to 6 carbon atoms as well as with alkenyl and alkynyl iodides of 3 to 6 carbon atoms to afford the corresponding 1-substituted precursors.

EXAMPLE 4

1-Methyl-1,2-Dihydro-2-Oxo-4-(1-Pyrrolidinyl)-1,8-Naphthyridine-3-Carboxylic Acid Ethyl Ester A stirred mixture of 2.7 g. (0.01 mole) of 4-chloro-1,2-dihydro-1-methyl-2-oxo-1,8-naphthyridine-3-carboxylic acid ethyl ester, 0.7 g. (0.01 mole) of pyrrolidine and 1.06 g. (0.01 mole) of sodium carbonate in 25 ml. of ethanol was heated under reflux for 5 hours. The mixture was filtered and the filtrate was cooled in ice. The precipitate which formed was collected and was dissolved in 20 ml. of ethyl acetate. The solution was diluted with petroleum ether to the cloudy point. The precipitate which formed was collected to yield 0.5 g. of product, m.p. 118°-120° C.

Analysis for: $C_{16}H_{19}N_3O_3$; Calculated: C, 63.77; H, 6.36; N, 13.95; Found: C, 63.46; H, 6.51; N, 14.01.; Percentage Inhibition: 55%.

EXAMPLE 5

1,7-Dimethyl-1,2-Dihydro-2-Oxo-4-(1-Pyrrolidinyl)-1,8-Naphthyridine-3-Carboxylic Acid Ethyl Ester A stirred mixture of 1 g. of 1,2-dihydro-1,7-dimethyl-4-hydroxy-2-oxo-1,8-naphthyridine-3-carboxylic acid, ethyl ester in 25 ml. of thionyl chloride was heated under reflux for 5 hours. The thionyl chloride was removed in a rotary evaporator and the residue was triturated with 10 ml. of ethyl acetate. The insoluble material was collected to give 0.8 g. of material. A small amount of this solid was recrystallized from ethyl acetate to give the analytical sample, m.p. 180°-184° C. of 4-chloro-1,2-dihydro-1,7-dimethyl-2-oxo-1,8-naphthyridine-3-carboxylic acid, ethyl ester.

Analysis for: $C_{13}H_{13}ClN_2O_3$; Calculated: C, 55.62; H, 4.67; N, 9.98; Found: C, 55.37; H, 4.60; N, 9.89.

A stirred mixture of 2.8 g. (0.01 mole) of 4-chloro-1,7-dimethyl-1,2-dihydro-2-oxo-1,8-naphthyridine-3-carboxylic acid ethyl ester, 0.7 g. (0.01 mole) of pyrrolidine and 1.06 g. (0.01 mole) of sodium carbonate in 30 ml. of ethanol was heated under reflux for 5 hours. The mixture was filtered and the filtrate was cooled in ice. The precipitate which formed was collected and was recrystallized from heptane to give 1.7 g. of product, m.p. 108°-111° C.

Analysis for: $C_{17}H_{21}N_3O_3$; Calculated: C, 64.74; H, 6.71; N, 13.33; Found: C, 64.78; H, 6.66; N, 13.40.; Percentage Inhibition: 78%.

EXAMPLE 6

1-Methyl-1,2-Dihydro-4-(4-Methyl-1-Piperazinyl)-2-Oxo-1,8-Naphthyridine-3-Carboxylic Acid Ethyl Ester A stirred mixture of 5.2 g. (0.02 mole) of 4-chloro-1,2-dihydro-1-methyl-2-oxo-1,8-naphthyridine-3-carboxylic acid ethyl ester, 2.0 g. (0.02 mole) of N-methylpiperazine and 2.12 g. (0.02 mole) of sodium carbonate was heated under reflux for 5 hours. The mixture was filtered and the filtrate was evaporated in a rotary evaporator. The residue was triturated with 50 ml. of a 20% aqueous sodium carbonate solution and was extracted with 50 ml. of ether. The ether layer was dried over magnesium sulfate, filtered, diluted with a few ml. of ethanol and was acidified with a saturated ethereal hydrochloric acid solution. The precipitate which formed was collected and was recrystallized from ethanol to afford 0.3 g. of product as the hydrochloride, hemihydrate, m.p. 231°–234° C. dec.

Analysis for: $C_{17}H_{23}ClN_4O_3 \cdot \frac{1}{2}H_2O$; Calculated: C, 54.33; H, 6.44; N, 14.91; Found: C, 54.19; H, 6.31; L N, 14.74. ; Percentage Inhibition: 74%.

EXAMPLE 7

1,7-Dimethyl-1,2-Dihydro-4-(4-Methyl-1-Piperazinyl)-2-Oxo-1,8-Naphthyridine-3-Carboxylic Acid Ethyl Ester A stirred mixture of 5.3 g. (0.019 mole) of 4-chloro-1,7-dimethyl-1,2-dihydro-2-oxo-1,8-naphthyridine-3-carboxylic acid ethyl ester, 1.9 g. (0.019 mole) of N-methylpiperazine and 1.9 g. (0.019 mole) of sodium carbonate in 100 ml. of ethanol was heated under reflux for 5 hours. The mixture was filtered and the filtrate was evaporated in a rotary evaporator. The residue was triturated with 150 ml. of 10% aqueous sodium carbonate and was extracted with 150 ml. of ether. The ether layer was dried over magnesium sulfate, filtered and was diluted with 30 ml. of ethanol. This solution was acidified with an ethereal hydrochloric acid solution. The precipitate which formed was collected and was recrystallized from ethanol to afford 1.0 g. of product as the hydrochloride, hemihydrate, m.p. 278°–280° C. dec.

Analysis for: $C_{18}H_2ClN_4O_3 \cdot HCl \cdot \frac{1}{2}H_2O$; Calculated: C, 55.45; H, 6.72; N, 14.37; Found: C, 55.66; H, 6.51; N, 14.50.; Percentage Inhibition: 98%.

EXAMPLE 8

4-Amino-1,2-Dihydro-1-Methyl-2-Oxo-1,8-Naphthyridine-3-Carboxylic Acid Ethyl Ester To a solution of 2.66 g. (0.02 mole) of 2-methylaminonicotinonitrile in 100 ml. of anhydrous ethyl ether was added 1.5 g. (0.01 mole) of ethyl malonyl chloride. After stirring at room temperature for 1 hour, the mixture was filtered. The filtrate was evaporated in a rotary evaporator and the residue was dissolved in 10 ml. of ethanol. This solution was added to a solution of 0.46 g. (0.02 g. atom) of sodium in 50 ml. of ethanol. After stirring for 5 minutes, the mixture was diluted with water and was acidified with conc. hydrochloric acid. The precipitate which formed was collected, air dried and was recrystallized from ethanol to afford 0.9 g. of product, m.p. 203°–206° C.

Analysis for: $C_{12}H_{13}N_3O_3$; Calculated: C, 58.29; H, 5.30; N, 17.00; Found: C, 57.96; H, 5.31; N, 17.16.; Percentage Inhibition: 86%.

EXAMPLE 9

4-Amino-1-Ethyl-1,2-Dihydro-2-Oxo-1,8-Naphthyridine-3-Carboxylic Acid Ethyl Ester Following the procedure of Taylor et al., J. Org. Chem., 19, 1633 (1954), a stirred mixture of 14 g. of nicotinamide N-oxide, 29.7 g. of phosphorus pentachloride and 40 ml. of phosphorus oxychloride was heated under reflux for 2 hours. The phosphorus oxychloride was evaporated in a rotary evaporator and the residue was poured over ice. The insoluble material was collected, air dried and was recrystallized from heptane to give 6.0 g. of 2-chloronicotinonitrile.

A stirred mixture of 4 g. of 2-chloronicotinonitrile in 200 ml. of a saturated ethanolic ethylamine solution was heated under reflux for 5 hours. The solution was cooled and was diluted with 400 ml. of water. The precipitate of 2-ethylaminonicotinonitrile which formed was collected, air dried and was used directly in the next step without further purification.

To a solution of 4.4 g. (0.03 mole) of 2-ethylaminonicotinonitrile in 200 ml. of anhydrous diethyl ether was added 2.25 g. (0.015 mole) of ethyl malonyl chloride. After stirring at room temperature for 2 hours, the mixture was filtered. The filtrate was evaporated in a rotary evaporator and the residue was dissolved in 20 ml. of ethanol. This solution was added to a solution of 0.69 g. (0.03 g. atom) of sodium in 100 ml. of ethanol. After stirring for 5 minutes at room temperature, the mixture was diluted with water and was acidified with conc. hydrochloric acid. The precipitate which formed was collected, air dried and was recrystallized from ethyl acetate to afford 1.8 g. of the title compound as a hemihydrate, m.p. 205°–208° C.

Alternatively, 4-Amino-1-ethyl-1,2-dihydro-2-oxo-1,8-naphthyridine-3-carboxylic acid ethyl ester may be prepared as follows:

To a solution of 2.07 g. (0.09 g. atom) of sodium in 75 ml. of absolute ethanol was added 14.4 g. (0.09 mole) of diethyl malonate. The solution was stirred at room temperature for 5 minutes. Then 4.4 g. (0.03 mole) of 2-ethylaminonicotinonitrile was added and the mixture was heated under reflux for 6 hours. The mixture was cooled and was diluted with 75 ml. of water and was acidified with concentrated hydrochloric acid. The precipitate which formed was collected and was dried to give 3.2 g. of material. Two recrystallizations from ethanol provided 1.1 g. of pure product, m.p. 203°–207° C.

A third method of preparing 4-amino-1-ethyl-1,2-dihydro-2-oxo-1,8-naphthyridine-3-carboxylic acid ethyl ester is as follows:

To a stirred solution of 0.026 mole of sodium ethoxide (0.6 g. sodium in 200 ml. of ethanol) was added 6 g. (0.025 mole) of 4-amino-1,2-dihydro-2-oxo-1,8-naphthyridine-3-carboxylic acid ethyl ester and 11.7 g. (0.075 mole) of ethyl iodide. The reaction mixture was heated under reflux for 4 hours; then filtered. The filtrate was taken to dryness and the residue was washed with water. The crude product amounted to 2.3 g., m.p. 194°–198° and gave no melting point depression on admixture with samples prepared as previously described.

Analysis for: $C_{13}H_{15}N_3O_3 \cdot \frac{1}{2}H_2O$; Calculated: C, 57.77; H, 5.97; N, 15.55; Found: C, 57.82; H, 5.97; N, 15.81.; Percentage Inhibition: 89%.

EXAMPLE 10

4-Amino-1-Ethyl-1,2-Dihydro-2-Oxo-1,8-Naphthyridine-3-Carboxylic Acid, n-Butyl Ester To a solution of 1.38 g. (0.06 g. atom) of sodium in 200 ml. of n-butyl alcohol was added 12.96 g. (0.06 mole) of di-n-butylmalonate. After stirring for 2 minutes, 8.82 g. (0.06 mole) of 2-ethylaminonicotinonitrile was added. The mixture was heated under reflux for 5 hours. The n-butyl alcohol was removed in a rotary evaporator and the residue was triturated with 250 ml. of a 20% aqueous hydrochloric acid solution. This mixture was extracted with 200 ml. of ethyl ether. The ether layer was dried over magnesium sulfate, filtered and the ether layer was acidified with an ethereal hydrochloric acid solution. The precipitate which formed was collected and this material was triturated with 100 ml. of a 10% aqueous sodium carbonate solution. The insoluble material was dissolved in ether. The ether layer was dried over magnesium sulfate, filtered and the ether was evaporated. The residue was recrystallized from ethyl acetate to afford 0.5 g. of product, m.p. 117°–120° C.

Analysis for: $C_{15}H_{19}N_3O_3$; Calculated: C,62.26; H, 6.62; N, 14.52; Found: C,61.96; H, 6.50; N, 14.74.; Percentage Inhibition: 85%.

EXAMPLE 11

4-Amino-1,2-Dihydro-1-Ethyl-2-Oxo-1,8-Naphthyridine-3-Carboxylic Acid Hydrazide A stirred mixture of 2 g. of 4-amino-1-ethyl-1,2-dihydro-2-oxo-1,8-naphthyridine-3-carboxylic acid ethyl ester in 20 ml. of ethanol containing 5 ml. of hydrazine was heated under reflux for 4 hours. The mixture was cooled and the insoluble material was collected. The filter cake was recrystallized from ethanol to produce 1.1 g. of product, m.p. 275°–277° C. dec.

Analysis for: $C_{11}H_{13}N_5O_2$; Calculated: C, 53.43; H, 5.30; N, 28.33; Found: C, 53.33; H, 5.47; N, 28.69.; Percentage Inhibition: 88%.

EXAMPLE 12

4-Amino-1-Ethyl-1,2-Dihydro-2-Oxo-1,8-Naphthyridine-3-Carboxylic Acid

A stirred mixture of 2 g. of 4-amino-1-ethyl-1,2-dihydro-2-oxo-1,8-naphthyridine-3-carboxylic acid ethyl ester in 20 ml. of 10% aqueous sodium hydroxide containing 5 ml. of ethanol was heated under reflux for 3 hours to saponify the ester. The solution was cooled and was acidified with glacial acetic acid. The precipitate which formed was collected, air dried, and was recrystallized from ethanol to give 0.4 g. of product, m.p. 245°–248° C.

Analysis for: $C_{11}H_{11}N_3O_3$; Calculated: C, 56.65; H, 4.75; N, 18.02; Found: C, 56.41; H, 4.80; N, 18.04; Percentage Inhibition: 76%.

Treatment of the free carboxylic acid with a stoichiometric amount of NaOH, KOH, NH4OH, diethylamine, and the like bases forms the corresponding carboxylic acid salt.

EXAMPLE 13

4-(Diacetylamino)-1-Ethyl-1,2-Dihydro-2-Oxo-1,8-Naphthyridine-3-Carboxylic Acid Ethyl Ester A stirred mixture of 6 g. of 4-amino-1-ethyl-1,2-dihydro-2-oxo-1,8-naphthyridine-3-carboxylic acid ethyl ester in 100 ml. of acetyl chloride was heated under reflux for 24 hours. The mixture was filtered and the filtrate was evaporated in a rotary evaporator. The residue was recrystallized from 20 ml. of ethyl acetate to afford 2.9 g. of product, m.p. 133°–135° C.

Analysis for: $C_{17}H_{19}N_3O_5$; Calculated: C, 59.12; H, 5.55; N, 12.17; Found: C, 59.05; H, 5.55; N, 12.56.; Percentage Inhibition: 47%.

EXAMPLE 14

1-Ethyl-1,2-Dihydro-4-(4-Methyl-1-Piperazinyl)-2-Oxo-1,8-Naphthyridine-3-Carboxylic Acid Ethyl Ester A stirred mixture of 4.2 g. (0.015 mole) of 1-ethyl-1,2-dihydro-4-chloro-2-oxo-1,8-naphthridine-3-carboxylic acid ethyl ester (prepared in the manner described in Example 30), 1.5 g. (0.015 mole) of N-methylpiperazine and 1.6 g. (0.015 mole) of sodium carbonate in 20 ml. of ethanol was heated under reflux for 5 hours. The mixture was filtered and the filtrate was evaporated in a rotary evaporator. The residue was triturated with 50 ml. of 20% aqueous sodium carbonate and this mixture was extracted with 50 ml. of diethyl ether. The ether layer was dried over magnesium sulfate, filtered and was diluted with 50 ml. of ethanol. This solution was slowly acidified with an ethereal hydrochloric acid solution. The precipitate which formed was collected and was recrystallized from ethanol to give 2.5 g. of product as the hydrochloride, m.p. 230°–233° C.

Analysis for: $C_{18}H_{25}ClN_4O_3$; Calculated: C, 56.76; H, 6.62; N, 14.71; Found: C, 56.49; H, 6.59; N, 14.50.; Percentage Inhibition: 94%.

EXAMPLE 15

4-Amino-1-Propyl-1,2-Dihydro-2-Oxo-1,8-Naphthyridine-3-Carboxylic Acid Ethyl Ester A stirred mixture of 2.76 g. (0.02 mole) of 2-chloronicotinonitrile prepared as in Example 9, 1.18 g. (0.02 mole) of propylamine and 2.12 g. (0.02 mole) of sodium carbonate in 25 ml. of ethanol was heated under reflux for 5 hours. The mixture was filtered and the filtrate was cooled in ice and was diluted with water to the cloudy point. The precipitate which formed was collected, air dried and was recrystallized three times from pentane to give 0.7 g. of 2-propylaminonicotinonitrile, m.p. 33°–35° C. which was used directly in the next step.

To a solution of 4.5 g. (0.028 mole) of 2-propylaminonicotinonitrile in 100 ml. of anhydrous diethyl ether was added 2.1 g. (0.014 mole) of ethyl malonyl chloride. The mixture was stirred at room temperature for 2 hours and was filtered. The filtrate was evaporated in a rotary evaporator and the residue was dissolved in 10 ml. of ethanol. This solution was added to a solution of 0.64 g. (0.028 g. atom) of sodium in 50 ml. of ethanol. After stirring for 10 minutes, the mixture was diluted with water and was acidified with conc. hydrochloric acid. The precipitate which formed was collected, air dried and was recrystallized from ethyl acetate to give 2.1 g. of the title compound, m.p. 165°–168° C.

Analysis for: $C_{14}H_{17}N_3O_3$; Calculated: C, 61.08; H, 6.22; N, 15.26; Found: C, 61.02; H, 6.04; N, 15.19.; Percentage Inhibition: 79%.

EXAMPLE 16

4-Amino-1-Isobutyl-1,2-Dihydro-2-Oxo-1,8-Naphthyridine-3-Carboxylic Acid Ethyl Ester A stirred mixture of 5 g. of 2-chloronicotinonitrile in 25 ml. of isobutylamine was heated under reflux for 30 minutes. The mixture was cooled and was diluted with water to the cloudy point. The precipitate which formed was collected, air dried and was recrystallized from heptane to give 4 g. of 2-isobutylaminonicotinonitrile, m.p. 80°–84° C.

Analysis for: $C_{10}H_{13}N_3$; Calculated: C, 68.54; H, 7.48; N, 23.98; Found: C, 68.93; H, 7.77; N, 24.24.

To a solution of 12.25 g. (0.07 mole) of 2-isobutylaminonicotinonitrile in 300 ml. of anhydrous ethyl ether was added 5.2 g. (0.035 mole) of ethyl malonyl chloride. The mixture was stirred at room temperature for 30 minutes and was filtered. The filtrate was evaporated in a rotary evaporator and the residue was dissolved in 20 ml. of ethanol. This solution was added to a solution of 1.6 g. of sodium in 150 ml. of ethanol. After stirring at room temperature for 5 minutes, the mixture was diluted with water and was acidified with conc. hydrochloric acid. The precipitate which formed was collected, air dried and was recrystallized from ethyl acetate to afford 2.1 g. of the title product, m.p. 157°–159° C.

Analysis for: $C_{15}H_{19}N_3O_3$; Calculated: C, 62.26; H, 6.62; N, 14.52; Found: C, 62.03; H, 6.55; N, 14.56.; Percentage Inhibition: 81%.

EXAMPLE 17

4-Amino-1-Cyclohexyl-1,2-Dihydro-2-Oxo-1,8-Naphthyridine-3-Carboxylic Acid Ethyl Ester A stirred mixture of 5 g. of 2-chloronicotinonitrile in 20 ml. of cyclohexylamine was heated under reflux for 30 minutes. The mixture was cooled and was diluted with water to the cloudy point. The precipitate which formed was collected, air dried and was recrystallized from heptane to give 2.0 g. of 2-cyclohexylaminonicotinonitrile, m.p. 87°–89° C.

Analysis for: $C_{12}H_{15}N_3$; Calculated: C, 71.61; H, 7.51; N, 20.88; Found: C, 71.55; H, 7.53; N, 20.93.

To a solution of 20.1 g. (0.1 mole) of 2-cyclohexylaminonicotinonitrile in 1000 ml. of anhydrous ethyl ether was added 7.5 g. (0.05 mole) of ethyl malonyl chloride. The mixture was stirred at room temperature for 1 hour. The mixture was filtered and the filtrate was evaporated in a rotary evaporator. The residue was triturated with 30 ml. of ether and was filtered. The filtrate was evaporated and this residue was added to a solution of 2.3 g. (0.1 g. atom) of sodium in 250 ml. of ethanol. The mixture was stirred at room temperature for 5 minutes, diluted with water and was acidified with conc. hydrochloric acid. The solution was cooled in ice and the precipitate which formed was collected, air dried and was recrystallized twice from ethyl acetate to afford 1.0 g. of the title product, m.p. 172°–175° C.

Analysis for: $C_{17}H_{21}N_3O_3$; Calculated: C, 64.74; H, 6.71; N, 13.33; Found: C, 64.36; H, 6.67; N, 12.99.; Percentage Inhibition: 68%.

EXAMPLE 18

1-Allyl-4-Amino-1,2-Dihydro-2-Oxo-1,8-Naphthyridine-3-Carboxylic Acid Ethyl Ester A stirred mixture of 13.3 g. (0.1 mole) of 2-chloronicotinonitrile prepared as in Example 9, 11.4 g. (0.2 mole) of allylamine and 10.6 g. (0.1 mole) of sodium carbonate in 200 ml. of ethanol was heated under reflux for 6 hours. The mixture was filtered and the filtrate was diluted with water to the cloudy point. The precipitate which formed was collected, air dried and was recrystallized from petroleum ether to give 10 g. of product. A small amount of this solid was recrystallized again from petroleum ether to give the analytical sample, m.p. 60°–62° C.

Analysis for: $C_9H_9N_3$; Calculated: C, 67.90; H, 5.70; N, 26.40; Found: C, 67.68; H, 5.66; N, 26.08.

To a solution of 9.5 g. (0.06 mole) of 2-allylaminonicotinonitrile in 30 ml. of anhydrous diethyl ether was added 4.5 g. (0.03 mole) of ethyl malonyl chloride. The mixture was stirred at room temperature for 3 hours and was filtered. The filtrate was evaporated in a rotary evaporator and the residue was dissolved in 20 ml. of ethanol and this solution was added to a solution of 1.38 g. (0.06 g. atom) of sodium in 200 ml. of ethanol. After stirring at room temperature for 10 minutes, the mixture was diluted with water and was acidified with concentrated hydrochloric acid. The precipitate which formed was collected, air dried and was recrystallized from ethyl acetate to afford 4.3 g. of the title compound, m.p. 161°–164° C.

Analysis for: $C_{14}H_{15}N_3O_3$; Calculated: C, 61.53; H, 5.53; N, 15.38; Found: C, 61.29; H, 5.52; N, 15.48.; Percentage Inhibition: 85%.

EXAMPLE 19

1-Allyl-1,2-Dihydro-7-Methyl-2-Oxo-4-(1-Pyrrolidinyl)-1,8-Naphthyridine-3-Carboxylic Acid Ethyl Ester A mixture of 26 g. of 2-hydroxy-6-methylnicotinic acid methyl ester obtained by the procedure of Mariella et al., JACS, 74, 1915 (1952) in 200 ml. of phosphorus oxychloride was heated under reflux for 6 hours. The phosphorus oxychloride was removed in a rotary evaporator and the residue was poured onto 1 liter of cracked ice. The mixture was extracted with 250 ml. of diethyl ether. The ether was dried over magnesium sulfate, filtered, and removed in a rotary evaporator to afford 18.0 g. of pure 2-chloro-6-methylnicotinic acid methyl ester.

Analysis for: $C_8H_8NClO_2$; Calculated: C, 51.77; H, 4.34; N, 7.55; Found: C, 51.67; H, 4.08; N 7.34.

A stirred mixture of 9.25 g. (0.05 mole) of methyl-2-chloro-6-methylnicotinate, 2.85 g. (0.05 mole) of allylamine and 5.3 g. (0.05 mole) of sodium carbonate in 50 ml. of ethanol was heated under reflux for 5 hours. The mixture was filtered and the filtrate was evaporated in a rotary evaporator. The residue was diluted with 50 ml. of water and was extracted with 50 ml. of diethyl ether. The ether layer was dried over magnesium sulfate, filtered and was evaporated. The residue was passed through a neutral aluminum oxide column using ethyl acetate as the eluent. Evaporation of the ethyl acetate gave 3.1 g. of product. A small amount of this oil was dissolved in diethyl ether containing a few drops of ethanol and this solution was acidified with an ethereal hydrochloric acid solution. The precipitate which formed was collected and was recrystallized from ethyl acetate to give 2-allylamino-6-methylnicotinic acid methyl ester hydrochloride hemihydrate, m.p. 140°–142° C.

Analysis for: $C_{11}H_{15}ClN_2O_2.\frac{1}{2}\ H_2O$; Calculated: C, 52.49; H, 6.42; N, 11.13; Found: C, 52.96; H, 5.94; N, 11.26.

To a solution of 2.88 g. (0.015 mole) of 2-allylamino-6-methylnicotinic acid, methyl ester in 50 ml. of anhydrous diethyl ether was added 1.12 g. (0.0075 mole) of ethyl malonyl chloride. The mixture was stirred at room temperature for 4 hours. The mixture was filtered and the filtrate was evaporated in a rotary evaporator. The residue was dissolved in 5 ml. of ethanol and this solution was added to a solution of 0.23 g. (0.01 g. atoms) of sodium in 20 ml. of ethanol. The mixture was diluted with water and was acidified with glacial acetic acid. The mixture was extracted with diethyl ether and the ether layer was dried over magnesium sulfate, filtered and was acidified with an ethereal hydrochloric acid solution. The mixture was filtered and the filtrate was evaporated. The residue was recrystallized from heptane to give 10 mg. of 1-allyl-1,2-dihydro-4-hydroxy-7-methyl-2-oxo-1,8-naphthyridine-3-carboxylic acid ethyl ester, m.p. 110°–112° C.

Analysis for: $C_{15}H_{16}N_2O_4$; Calculated: C, 62.49; H, 5.59; N, 9.72; Found: C, 62.22; H, 5.49; N, 9.62.

A stirred mixture of 1 g. of 1-allyl-1,2-dihydro-4-hydroxy-7-methyl-2-oxo-1,8-naphthyridine in 20 ml. of phosphorus oxychloride was heated under reflux for 2 hours. The phosphorus oxychloride was evaporated in a rotary evaporator and the residue was poured into 100 ml. of ice water. After cooling in ice for 1 hour, the solid was collected, air dried and was recrystallized from heptane to give 0.5 g. of 1-allyl-4-chloro-1,2-dihydro-7-methyl-2-oxo-1,8-naphthridine-3-carboxylic acid ethyl ester, m.p. 80°–82° C.

Analysis for: $C_{15}H_{15}ClN_2O_3$; Calculated: C, 58.73; H, 4.93; N, 9.13; Found: C, 58.33; H, 4.66; N, 9.11.

A stirred mixture of 0.49 g. (0.0016 mole) of 1-allyl-4-chloro-1,2-dihydro-7-methyl-2-oxo-1,8-naphthridine-3-carboxylic acid ethyl ester, 0.11 g. (0.0016 mole) of pyrrolidine and 0.16 g. (0.0016 mole) sodium carbonate in 20 ml. of ethanol was heated under reflux for 5 hours. The mixture was filtered and the filtrate was diluted with water to the cloudy point. The precipitate which formed was collected, air dried and was recrystallized from heptane to give 0.2 g. of the title compound, m.p. 97°–103° C.

Analysis for: $C_{19}H_{23}N_3O_3$; Calculated: C, 66.84; H, 6.79; N. 12.31; Found: C, 66.73; H, 6.88; N, 12.28.; Percentage Inhibition: 46%.

EXAMPLE 20

4-[(Chloroacetyl)Amino]-1,2-Dihydro-2-Oxo-1-(2-Propenyl)-1,8-Naphthyridine-3-Carboxylic Acid A stirred mixture of 4 g. of 1-allyl-4-amino-1,2-dihydro-2-oxo-1,8-naphthyridine-3-carboxylic acid ethyl ester in 30 ml. of chloroacetyl chloride was heated under reflux for 1 hour. The chloroacetyl chloride was evaporated in a rotary evaporator and the residue was triturated with 20 ml. of ethyl acetate. The insoluble material was collected and was recrystallized from ethyl acetate to give 1.2 g. of product, m.p. 145°–148° C.

Analysis for: $C_{14}H_{12}ClN_3O_4$; Calculated: C, 52.33; H, 3.77; N, 13.08; Found: C, 51.99; H, 3.75; N, 13.15.; Percentage Inhibition: 41%.

EXAMPLE 21

1-Ethyl-1,2-Dihydro-4-Trifluoroacetylamino-2-Oxo-1,8-Naphthyridine-3-Carboxylic Acid Ethyl Ester A stirred solution of 0.5 g. (0.002 mole) of 4-amino-1-ethyl-1,2-dihydro-2-oxo-1,8-naphthyridine-3-carboxylic acid ethyl ester in 20 ml. of trifluoroacetic anhydride was heated under reflux for 3 hours. The reaction solution was cooled in ice and filtered. There was obtained 0.3 g. of product, m.p. 195°–197° C.

Analysis for: $C_{15}H_{14}F_3N_3O_4$; Calculated: C, 50.42; H, 3.94; N, 11.76; Found: C, 50.25; H, 3.91; N, 11.77; Percentage Inhibition: 88%.

EXAMPLE 22

1-Propargyl-4-Amino-2-Oxo-1,8-Naphthyridine-3-Carboxylic Acid Ethyl Ester

The title compound is produced following the procedure of Example 18 with the exception that propargylamine is employed as an initial reactant rather than allylamine.

EXAMPLE 23

4-Amino-7-Chloro-1-Ethyl-1,2-Dihydro-2-Oxo-1,8-Naphthyridine-3-Carboxylic Acid Ethyl Ester To a solution of 2.07 g. (0.09 g. atom) of sodium in 75 ml. of ethanol is added 14.4 g. (0.09 mole) of diethyl malonate. The solution is stirred at room temperature for 5 minutes and then 5.4 g. (0.03 mole) of 6-chloro-2-ethylaminonicotinonitrile is added. The mixture is heated under reflux for about 6 hours. The mixture is cooled and diluted with 75 ml. of water and acidified with conc. hydrochloric acid. The precipitate which forms is collected and air dried to give the title compound.

EXAMPLE 24

4-Amino-7-Ethoxy-1-Ethyl-1,2-Dihydro-2-Oxo-1,8-Naphthyridine-3-Carboxylic Acid Ethyl Ester To 50 ml. of absolute ethanol is added 0.46 g. of sodium. After all the sodium has reacted, the solution is taken to dryness in a rotary evaporator. Dimethyl formamide (100 ml.) is added, followed by 3 g. of 4-amino-7-chloro-1-ethyl-1,2-dihydro-2-oxo-1,8-naphthyridine-3-carboxylic acid ethyl ester. The reaction mixture is heated under reflux for several hours. The dimethyl formamide is removed in a rotary evaporator. Water (20 ml.) is added and the mixture is neutralized with acetic acid. The product is recovered by filtration.

EXAMPLE 25

4-Amino-1,N-Diethyl-7-Ethylamino-1,2-Dihydro-2-Oxo-1,8-Naphthyridine-3-Carboxamide To 20 g. of a 70% aqueous ethylamine solution in an autoclave is added 5 g. of 4-amino-7-chloro-1-ethyl-1,2-dihydro-2-oxo-1,8-naphthyridine-3-carboxylic acid ethyl ester. Ethanol (20 ml.) is added and the reaction mixture is heated to about 170° C. overnight. The reaction mixture is cooled and filtered and the product collected.

EXAMPLE 26

4-Amino-1-Ethyl-1,2-Dihydro-7-Methyl-2-Oxo-1,8-Naphthyridine-3-Carboxylic Acid Ethyl Ester Following the procedure of Perez-Medina et al., J. Am. Chem. Soc., 69, 2574 (1947), a stirred mixture of 8 g. of 2-hydroxy-6-methylnicotinonitrile in 50 ml. of phosphorus oxychloride was heated under reflux for 2 hours. The phosphorus oxychloride was evaporated in a rotary evaporator and the residue was poured onto 100 g. of ice. The precipitate which formed was collected and air dried to give 6.0 g. of 2-chloro-6-methylnicotinitrile, m.p. 105°–110° C.

A stirred mixture of 6 g. of 2-chloro-6-methylnicotinonitrile in 100 ml. of a saturated ethanolic ethylamine solution was heated under reflux for 6 hours. The solution was cooled and was diluted with water to give 4.0 g. of 2-ethylamino-6-methylnicotinonitrile, m.p. 64°–67° C. This material was used directly in the next step without further purification.

To a solution of 4.0 g. (0.025 mole) of 2-ethylamino-6-methylnicotinonitrile in 100 ml. of anhydrous diethyl ether was added 1.88 g. (0.0125 mole) of ethyl malonyl chloride. The mixture was stirred at room temperature for 1 hour and was filtered. The filtrate was evaporated in a rotary evaporator and the residue was dissolved in 10 ml. of ethanol and this solution was added to a solution of 0.575 g (0.025 g. atom) of sodium in 50 ml. of ethanol. After stirring for 5 minutes, the mixture was diluted with water and was acidified with conc. hydrochloric acid. The precipitate which formed was collected, air dried and was recrystallized from ethyl acetate to give 0.8 g. of the title compound, m.p. 196°–198° C.

Analysis for: $C_{14}H_{17}N_3O_3$; Calculated: C, 61.08; H, 6.22; N, 15.26; Found: C, 60.96; H, 6.18; N, 15.35.; Percentage Inhibition: 76%.

EXAMPLE 27

4-Amino-1-Ethyl-1,2-Dihydro-7-Methyl-2-Oxo-1,8-Naphthyridine-3-Carbonitrile

To a cold solution of 5.4 g. (0.12 mole) of anhydrous ethylamine in 5 ml. of ethanol was added 11.1 g. (0.06 mole) of 2-chloro-6-methylnicotinic acid methyl ester (Example 19). The mixture was heated in a glass autoclave over a steam bath for 5 hours. The mixture was then evaporated in a rotary evaporator and the residue was added to 100 ml. of water and was basified with conc. ammonium hydroxide. The mixture was then extracted with 100 ml. of chloroform. The chloroform layer was dried over magnesium sulfate, filtered and was evaporated to give 2-ethylamino-6-methylnicotinic acid methyl ester as an oil which was used without further purification.

For characterization purposes, a hydrochloride was prepared by dissolving a few ml. of free base in ethyl acetate and adding dropwise a saturated solution of hydrogen chloride in diethyl ether. A few drops of ethanol was added. The solid which formed was removed by filtration and recrystallized from ethyl acetate-ethanol and dried in vacuo at 56° C. (m.p. 123°–125° C.).

Analysis for: $C_{10}H_{15}ClN_2O_2$; Calculated: C, 52.06; H, 6.12; N, 12.15; Found: C, 51.69; H, 6.44; N, 12.00.

To a solution of 3.98 g. (0.02 mole) of 2-ethyl-amino-6-methylnicotinic acid methyl ester in 50 ml. of anhydrous diethyl ether was added 1.5 g. (0.01 mole) of ethyl malonyl chloride. The mixture was stirred at room temperature for 1 hour. The mixture was filtered and the filtrate was evaporated in a rotary evaporator. The residue was added to a solution of 0.23 g. of sodium in 50 ml. of absolute ethanol and was warmed for 5 minutes. The mixture was cooled and the insoluble material was collected and was dissolved in water. Acidification of the water solution with glacial acetic acid afforded a precipitate which was collected, air dried and was recrystallized from heptane to give 1.2 g. of 1-ethyl-1,2-dihydro-4-hydroxy-7-methyl-2-oxo-1,8-naphthyridine-3-carboxylic acid ethyl ester, m.p. 147°–151° C.

Analysis for: $C_{14}H_{16}N_2O_4$; Calculated: C, 60.86; H, 5.84; N, 10.14; Found: C, 60.88; H, 6.00; N, 9.99.

To 1 g. of 1-ethyl-1,2-dihydro-4-hydroxy-7-methyl-2-oxo-1,8-naphthyridine-3-carboxylic acid ethyl ester was added 20 g. of phosphorus pentachloride. The reaction became exothermic. After 10 minutes, heat was applied to the reaction and the mixture was kept under reflux for 1 hour. The hot solution was poured onto 100 ml. of ice and the mixture was extracted with 50 ml. of diethyl ether. The ether layer was dried over magnesium sulfate, filtered and was evaporated in a rotary evaporator. The residue was recrystallized from ethyl acetate to afford 0.1 g. of 4-chloro-1-ethyl-7-methyl-3-(trichloromethyl)-1,8-naphthyridin-2-(1H)-one, m.p. 158°–160° C.

Analysis for: $C_{12}H_{10}Cl_4N_2O$; Calculated: C, 42.38; H, 2.96; N, 8.24; Found: C, 42.62; H, 3.04; N, 8.26.

A stirred mixture of 7.5 g. of 4-chloro-1-ethyl-7-methyl-3-(trichloromethyl)-1,8-naphthyridin-2-(1H)-one was heated under reflux in 200 ml. of a saturated ethanolic ammonia solution for 6 hours. The mixture was cooled and the precipitate which formed was collected and was recrystallized twice from ethanol to give 0.3 g. of the title compound, m.p. >300° C.

Analysis for: $C_{12}H_{12}N_4O$; Calculated: C, 63.14; H, 5.30; N, 24.55; Found: C, 62.96; H, 5.47; N, 24.64.; Percentage Inhibition: 53%.

EXAMPLE 28

4-Amino-1-Ethyl-1,2-Dihydro-7-Methyl-2-Oxo-1,8-Naphthyridine-3-Carboxamide

The reaction filtrate from the previous example was diluted with water. The precipitate which formed was collected, air dried and was recrystallized from ethanol to give 0.2 g. of product, m.p. 263°–266° C.

Analysis for: $C_{12}N_{14}N_4O_2$; Calculated: C, 58.52; H, 5.73; N, 22.75; Found: C, 58.38; H, 5.39; N, 22.37.; Percentage Inhibition: 57%.

EXAMPLE 29

1-Ethyl-1,2-Dihydro-7-Methyl-2-Oxo-4-(1-Pyrrolidinyl)-1,8-Naphthyridine-3-Carbonitrile A mixture of 1 g. of 1-ethyl-1,2-dihydro-4-hydroxy-7-methyl-2-oxo-1,8-naphthyridine-3-carboxylic acid ethyl ester (Example 27) in 20 ml. of a saturated ethanolic ammonia solution was heated in an autoclave placed in a steam bath for 4 hours. The mixture was cooled and was filtered. The filter cake was triturated with 50 ml. of a 20% aqueous acetic acid solution. The insoluble material was collected, air dried and was recrystallized from ethanol to afford 0.4 g. of 1-ethyl-1,2-dihydro-4-hydroxy-7-methyl-2-oxo-1,8-naphthyridine-3-carboxamide, m.p. 240°–242° C.

Analysis for: $C_{12}H_{13}N_3O_3$; Calculated: C, 58.29; H, 5.30; N, 17.00; Found: C, 57.92; H, 5.52; N, 16.91.

A stirred mixture of 10 g. of 1-ethyl-1,2-dihydro-4-hydroxy-7-methyl-2-oxo-1,8-naphthyridine-3-carboxamide in 200 ml. of phosphorus oxychloride was heated under reflux for 3 hours. The phosphorus oxychloride was evaporated in a rotary evaporator. To this residue was quickly added 400 ml. of ice water. The insoluble material was collected, air dried and was recrystallized from ethanol to give 5.5 g. of 4-chloro-1-ethyl-1,2-dihydro-7-methyl-2-oxo-1,8-naphthyridine-3-carbonitrile, m.p. 215°–217° C.

Analysis for: $C_{12}H_{10}ClN_3O$; Calculated: C, 58.19; H, 4.07; N, 16.96; Found: C, 57.93; H, 4.24; N, 16.31.

A stirred mixture of 7.41 g. (0.03 mole) of 4-chloro-1-ethyl-1,2-dihydro-7-methyl-2-oxo-1,8-naphthyridine-3-carbonitrile, 2.13 g. (0.03 mole) of pyrrolidine and 3.18 g. (0.03 mole) of sodium carbonate in 100 ml. of ethanol was heated under reflux for 1 hour. The mixture was filtered and the filter cake was triturated with 200 ml. of water. The insoluble material was collected, air dried and was recrystallized from 2-ethoxyethanol to give 7.4 g. of the title product, m.p. 211°–213° C.

Analysis for: $C_{16}H_{18}N_4O$; Calculated: C, 68.06; H, 6.43; N, 19.85; Found: C, 68.24; H, 6.57; N, 19.84.; Percentage Inhibition: 41%.

EXAMPLE 30

1-Ethyl-1,2-Dihydro-7-Methyl-2-Oxo-4-(1-Pyrrolidinyl)-1,8-Naphthridine-3-Carboxylic Acid Ethyl Ester A stirred mixture of 1 g. of 1-ethyl-1,2-dihydro-4-hydroxy-7-methyl-2-oxo-1,8-naphthyridine-3-carboxylic acid ethyl ester (Example 27) in 20 ml. of thionyl chloride was heated under reflux for 3 hours. The thionyl chloride was removed in a rotary evaporator and the residue was recrystallized from ethyl acetate to give 0.3 g. of 4-chloro-1-ethyl-1,2-dihydro-7-methyl-2-oxo-1,8-naphthyridine-3-carboxylic acid ethyl ester, m.p. 143°–145° C.

Analysis for: $C_{14}H_{15}ClN_2O_3$; Calculated: C, 57.05; H, 5.13; N, 9.51; Found: C, 57.21; N, 4.93; N, 9.55.

Alternatively, 4-chloro-1-ethyl-1,2-dihydro-7-methyl-2-oxo-1,8-naphthyridine-3-carboxylic acid ethyl ester may be prepared as follows:

To a solution of 27.5 g. (0.1 mole) of 4-amino-1-ethyl-1,2-dihydro-7-methyl-2-oxo-1,8-naphthyridine-3-carboxylic acid ethyl ester in 500 ml. of concentrated hydrochloric acid was added, dropwise over 5 minutes, a solution of 34.5 g. (0.5 mole) of sodium nitrite in 60 ml. of water. The mixture was stirred at room temperature for 30 minutes and was then poured into 1000 ml. of cold water. The insoluble material was collected, air dried and was recrystallized from ethyl acetate to give 20.0 g. of product, m.p. 144°–146° C.

A stirred mixture of 5.9 g. (0.02 mole) of 1-ethyl-1,2-dihydro-4-chloro-7-methyl-2-oxo-1,8-naphthyridine-3-carboxylic acid ethyl ester, 1.4 g. (0.02 mole) of pyrrolidine and 2.12 g. (0.02 mole) of sodium carbonate was heated under reflux in 50 ml. of ethanol for 3 hours. The mixture was filtered and the filtrate was diluted with water to the cloudy point. The precipitate which formed was collected, air dried and was recrystallized from heptane to give 3.3 g. of the title compound, m.p. 113°–115° C.

Analysis for: $C_{18}H_{23}N_3O_3$; Calculated: C, 65.63; H, 7.04; N, 12.76; Found: C, 65.67; H, 6.97; N, 12.82.; Percentage Inhibition: 83%.

EXAMPLE 31

4-Diethylamino-1-Ethyl-1,2-Dihydro-7-Methyl-2-Oxo-1,8-Naphthyridine-3-Carboxylic Acid Ethyl Ester A mixture of 1.47 g. (0.005 mole) of 1-ethyl-1,2-dihydro-4-chloro-7-methyl-2-oxo-1,8-naphthyridine-3-carboxylic acid ethyl ester (Example 30) and 0.7 g. (0.01 mole) of diethylamine in 20 ml. of ethanol was heated in an autoclave placed in a steam bath for 16 hours. The solution was then evaporated in a rotary evaporator and the residue was triturated with 50 ml. of water and was extracted with 50 ml. of diethyl ether. The ether layer was dried over magnesium sulfate, filtered and was evaporated in a rotary evaporator. The residue was recrystallized from heptane. A second recrystallization from petroleum ether gave 0.4 g. of product, m.p. 79°–82° C.

Analysis for: $C_{18}H_{25}N_3O_3$; Calculated: C, 65.23; H, 7.60; N, 12.68; Found: C, 64.89; H, 7.40; N, 12.58.; Percentage Inhibition: 50%.

EXAMPLE 32

1-Ethyl-1,2-Dihydro-7-Methyl-4-(4-Morpholinyl)-2-Oxo-1,8-Naphthyridine-3-Carboxylic Acid Ethyl Ester A stirred mixture of 0.59 g. (0.002 mole) of 1-ethyl-1,2-dihydro-4-chloro-7-methyl-2-oxo-1,8-naphthyridine-3-carboxylic acid ethyl ester (Example 30), 0.17 g. (0.002 mole) of morpholine and 0.2 g. (0.002 mole) of sodium carbonate in 20 ml. of ethanol was heated under reflux for 4 hours. The mixture was filtered and the filtrate was diluted with water to the cloudy point. The precipitate which formed was collected, air dried and was recrystallized from heptane to afford 0.2 g. of product, m.p. 129°–131° C.

Analysis for: $C_{18}H_{23}N_3O_4$; Calculated: C, 62.52; H, 6.71; N, 12.17; Found: C, 62.47; H, 6.46; N, 11.99.; Percentage Inhibition: 88%.

EXAMPLE 33

1-Ethyl-1,2-Dihydro-7-Methyl-4-(4-Methyl-1-Piperazinyl)-2-Oxo-1,8-Naphthyridine-3-Carboxylic Acid Ethyl Ester Hydrochloride A stirred mixture of 5.8 g. (0.02 mole) of 1-ethyl-1,2-dihydro-4-chloro-7-methyl-2-oxo-1.8-naphthyridine-3-carboxylic acid ethyl ester (Example 30), 2.0 g. (0.02 mole) of N-methylpiperazine and 2.12 g. (0.02 mole) of sodium carbonate in 50 ml. of ethanol was heated under reflux for 6 hours. The mixture was filtered and the filtrate was evaporated in a rotary evaporator. The residue was triturated with 50 ml. of 20% sodium carbonate and was extracted with 75 ml. of diethyl ether. The ether layer was dried over magnesium sulfate, filtered and was diluted with 50 ml. of ethanol. This solution was acidified with an ethereal hydrochloric acid solution and the precipitate which formed was collected and was recrystallized from ethanol to give 3.2 g. of product, m.p. 285°–288° C. dec.

Analysis for: $C_{19}H_{27}N_4O_3Cl$; Calculated: C, 57.59; H, 6.89; N, 14.19; Found: C, 57.74; H, 7.04; N. 14.27.; Percentage Inhibition: 85%.

The product of the preceding paragraph was converted to it's free base with excess sodium carbonate and then saponified with a stoichiometric amount of sodium hydroxide to yield the sodium salt of the carboxylic acid. Similarly, the ethyl ester may be saponified with a stoichiometric amount of potassium hydroxide. Other salts may be produced directly from the free carboxylic acid by conventional means.

EXAMPLE 34

1-Ethyl-1,2-Dihydro-7-Methyl-2-Oxo-4-(4-Phenyl-1-Piperazinyl)-1,8-Naphthyridine-3-Carboxylic Acid Ethyl Ester A stirred mixture of 5.9 g. (0.02 mole) of 1-ethyl-1,2-dihydro-4-chloro-7-methyl-2-oxo-1,8-naphthyridine-3-carboxylic acid ethyl ester (Example 30), 3.24 g. (0.02 mole) of sodium carbonate was heated under reflux in 50 ml. of ethanol for 3 hours. The mixture was filtered and the filtrate was diluted with water to the cloudy point. The precipitate which formed was collected, air dried and was recrystallized twice from ethyl acetate-petroleum ether. A third recrystallization from hexane gave 0.2 g. of product, m.p. 110°–112° C.

Analysis for: $C_{24}H_{28}N_4O_3$; Calculated: C, 68.55; H, 6.71; N, 13.33; Found: C, 68.34; H, 6.64; N, 13.35.

EXAMPLE 35

1-Ethyl-1,2-Dihydro-4-[(2-Hydroxyethyl)Methylamino]-7-Methyl-2-Oxo-1,8-Naphthyridine-3-Carboxylic Acid Ethyl Ester A stirred mixture of 1.47 g. (0.005 mole) of 1-ethyl-1,2-dihydro-4-chloro-7-methyl-2-oxo-1,8-naphthyridine-3-carboxylic acid ethyl ester (Example 30), 0.38 g. (0.005 mole) of 2-methylaminoethanol and 0.53 g. (0.005 mole) of sodium carbonate in 20 ml. of ethanol was heated under reflux for 5 hours. The mixture was filtered and the filtrate was diluted with water to the cloudy point. The precipitate which formed was collected, air dried and was recrystallized from ethyl acetate to afford 0.5 g. of product, m.p. 111°–113° C.

Analysis for: $C_{17}H_{23}N_3O_4$; Calculated: C, 61.24; H, 6.95; N, 12.61; Found: C, 61.09; H, 6.81; N, 12.63.; Percentage Inhibition: 52%.

EXAMPLE 36

1-Ethyl-1,2-Dihydro-4-(3-Dimethylaminopropylamino)-7-Methyl-2-Oxo-1,8-Naphthyridine-3-Carboxylic Acid Ethyl Ester A stirred mixture of 8.7 g. (0.03 mole) of 1-ethyl-1,2-dihydro-4-chloro-7-methyl-2-oxo-1,8-naphthyridine-3-carboxylic acid ethyl ester, (Example 30) 3.06 g. (0.03 mole) of 3-dimethylaminopropylamine and 3.18 g. of sodium carbonate in 100 ml. of ethanol was heated under reflux for 5 hours. The mixture was filtered and the filtrate was evaporated in a rotary evaporator. The residue was triturated with 150 ml. of water and was extracted with 150 ml. of diethyl ether. The ether layer was dried over magnesium sulfate, filtered and the ether was evaporated. The residue was passed through a neutral aluminum oxide column using ethyl acetate as the eluent. The ethyl acetate was evaporated and the residue was dissolved in anhydrous diethyl ether and the solution was acidified with an ethereal hydrochloric acid solution. The precipitate which formed was collected and was dried to give 1.9 g. of product as the hydrochloride, monohydrate, m.p. 75° C.

Analysis for: $C_{19}H_{31}ClN_4O_4$; Calculated: C, 55.00; H, 7.53; N, 13.50; Found: C, 55.25; H, 7.37; N, 13.59.; Percentage Inhibition: 32%.

EXAMPLE 37

1-Ethyl-1,2-Dihydro-4-Ethylamino-7-Methyl-2-Oxo-1,8-Naphthyridine-3-Carboxylic Acid Ethyl Ester A stirred mixture of 5.88 g. (0.02 mole) of 1-ethyl-1,2-dihydro-4-chloro-7-methyl-2-oxo-1,8-naphthyridine-3-carboxylic acid ethyl ester (Example 30) and 2.6 g. (0.04 mole) of 70% aqueous ethyl amine in 25 ml. of ethanol was heated under reflux for 5 hours. The solution was cooled and was diluted with water to the cloudy point. The precipitate which formed was collected, air dried, and was recrystallized from heptane to give 1.6 g. of product, m.p. 133°–136° C.

Analysis for: $C_{16}H_{21}N_3O_3$; Calculated: C, 63.35; H, 6.98; N, 13.85; Found: C, 63.25; H, 7.19; N, 13.87.; Percentage Inhibition: 70%.

EXAMPLE 38

1-Ethyl-1,2-Dihydro-7-Methyl-2-Oxo-4-(1-Piperazinyl)-1,8-Naphthyridine-3-Carboxylic Acid Ethyl Ester A stirred mixture of 1.47 g. (0.005 mole) of 1-ethyl-1,2-dihydro-4-chloro-7-methyl-2-oxo-1,8-naphthyridine-3-carboxylic acid ethyl ester (Example 30) and 1.72 g. (0.02 mole) of piperazine in 20 ml. of ethanol was heated under reflux for 5 hours. The mixture was filtered and the filtrate was diluted with 100 ml. of water and was extracted with 50 ml. of diethyl ether. The ether layer was dried over magnesium sulfate, filtered and was evaporated in an evaporating dish at room temperature. The residue was recrystallized from heptane to give 0.3 g. of product, m.p. 137°–139° C.

Analysis for: $C_{18}H_{24}N_4O_3$; Calculated: C, 62.77; H, 7.02; N, 16.27; Found: C, 62.76; H, 6.83; N. 16.12.; Percentage Inhibition: 98%.

EXAMPLE 39

4,4-(1,4-Piperazinediyl)Bis[1-Ethyl-1,2-Dihydro-7-Methyl-2-Oxo-1,8-Naphthyridine-3-Carboxylic Acid]Diethyl Ester A stirred mixture of 0.34 g. (0.001 mole) of 1-ethyl-1,2-dihydro-7-methyl-2-oxo-4-(1-piperazinyl)-1,8-naphthyridine-3-carboxylic acid ethyl ester (Example 38), 0.29 g. (0.001 mole) of 1-ethyl-1,2-dihydro-4-chloro-7-methyl-2-oxo-1,8-naphthyridine-3-carboxylic acid ethyl ester (Example 30) and 0.1 g. (0.001 mole) of sodium carbonate in 20 ml. of ethanol was heated under reflux for 4 hours. The mixture was filtered and the filter cake was triturated with 100 ml. of water. The insoluble material was collected, air dried and was recrystallized from 2-ethoxyethanol to give 0.1 g. of product, m.p. 264°–267° C.

Analysis for: $C_{32}H_{38}N_6O_6$; Calculated: C, 63.77; H, 6.36; N, 13.95; Found: C, 63.38; H, 6.22; N, 13.75.; Percentage Inhibition: 21%.

EXAMPLE 40

1-Ethyl-1,2-Dihydro-4-(4-Carbethoxy-1-Piperazinyl)-7-Methyl-2-Oxo-1,8-Naphthyridine-3-Carboxylic Acid Ethyl Ester A stirred mixture of 2.9 g. (0.01 mole) of 1-ethyl-1,2-dihydro-4-chloro-7-methyl-2-oxo-1,8-naphthyridine-3-carboxylic acid ethyl ester, 1.58 g. (0.01 mole) of ethyl N-piperazino-carboxylate, and 1.06 g. (0.01 mole) of sodium carbonate in 25 ml. of ethanol was heated under reflux for 6 hours. The mixture was filtered and the filtrate was diluted with a little water. The precipitate which formed was collected. The filtrate was further diluted with water and was left at room temperature overnight. This precipitate which formed was collected and was combined with the first crop. The combined crops were recrystallized from ethyl acetate to afford 0.5 g. of product, m.p. 138°-140° C.

Analysis for: $C_{21}H_{28}N_4O_5$; Calculated: C, 60.56; H, 6.78; N, 13.45; Found: C, 60.47; H, 7.04; N, 13.53.

What is claimed is:

1. A compound of the formula:

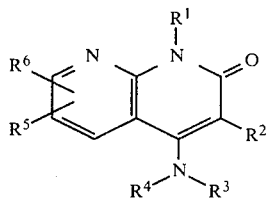

in which

R$^1$ is hydrogen, alkyl of 1 to 6 carbon atoms, cycloalkyl of 5 to 6 carbon atoms, alken-(3,4,5 or 6)-yl of 3 to 6 carbon atoms or alkyn-(3,4,5 or 6)-yl of 3 to 6 carbon atoms;

R$^2$ is —CN, —CO$_2$H, —CO$_2$R$^7$ where R$^7$ is alkyl of 1 to 6 carbon atoms, —CONHNH$_2$ or

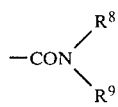

where R$^8$ and R$^9$ are independently hydrogen or alkyl of 1 to 6 carbon atoms;

R$^3$ and R$^4$ are independently hydrogen, alkyl of 1 to 6 carbon atoms, hydroxyalkyl of 1 to 6 carbon atoms, dialkylaminoalkyl of 4 to 8 carbon atoms, alkanoyl of 2 to 4 carbon atoms, haloalkanoyl of 2 to 4 carbon atoms, or when taken together with the nitrogen atom to which they are attached, R$^3$ and R$^4$ complete a heterocyclic group selected from aziridinyl, azetidinyl, pyrrolidinyl, piperidinyl, piperazinyl, 4-lower alkyl-piperazinyl, 4-phenyl-piperazinyl, 4-[1-ethyl-1,2-dihydro-7-methyl-2-oxo-1,8-naphthyridine-4-yl-3-carboxylic acid ethyl ester]piperazinyl, 4-carb(lower)alkoxy-piperazinyl, morpholinyl, thiomorpholinyl or a ring substituted lower alkyl analogue thereof;

R$^5$ and R$^6$ are independently hydrogen; alkyl of 1 to 4 carbon atoms, halo, alkylamino of 1 to 4 carbon atoms, or alkoxy of 1 to 6 carbon atoms;

or a pharmaceutically acceptable salt thereof.

2. A compound of claim 1 of the formula:

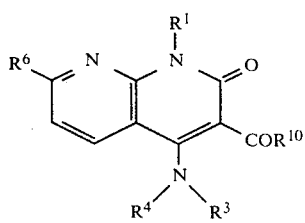

in which

R$^1$ is hydrogen, methyl, ethyl, propyl, allyl, propargyl, cyclohexyl, or isobutyl;

R$^3$ is hydrogen, alkyl of 1 to 6 carbon atoms or trifluoroacetyl;

R$^4$ is hydrogen, alkyl of 1 to 6 carbon atoms, or when taken with R$^3$ and the nitrogen atom to which they are attached, forms a heterocyclic group selected from pyrrolidinyl, morpholinyl, piperazinyl or 4-methylpiperazinyl;

R$^6$ is hydrogen or methyl; and

R$^{10}$ is hydroxy, alkoxy or 1 to 6 carbon atoms or hydrazinyl; or a pharmaceutically acceptable salt thereof.

3. The compound of claim 1 which is 4-amino-1,2-dihydro-2-oxo-1,8-naphthyridine-3-carboxylic acid ethyl ester.

4. The compound of claim 1 which is 4-amino-1,2-dihydro-2-oxo-1,8-naphthyridine-3-carboxylic acid or a pharmaceutically acceptable salt thereof.

5. The compound of claim 1 which is 1-methyl-4-(1-pyrrolidinyl)-1,2-dihydro-2-oxo-1,8-naphthyridine-3-carboxylic acid ethyl ester.

6. The compound of claim 1 which is 1,7-dimethyl-4-(1-pyrrolidinyl)-1,2-dihydro-2-oxo-1,8-naphthyridine-3-carboxylic acid ethyl ester.

7. The compound of claim 1 which is 1-methyl-4-(4-methyl-1-piperazinyl)-1,2-dihydro-2-oxo-1,8-naphthyridine-3-carboxylic acid ethyl ester.

8. The compound of claim 1 which is 1,7-dimethyl-4-(4-methyl-1-piperazinyl)-1,2-dihydro-2-oxo-1,8-naphthyridine-3-carboxylic acid ethyl ester.

9. The compound of claim 1 which is 4-amino-1-methyl-1,2-dihydro-2-oxo-1,8-naphthyridine-3-carboxylic acid ethyl ester.

10. The compound of claim 1 which is 4-amino-1-ethyl-1,2-dihydro-2-oxo-1,8-naphthyridine-3-carboxylic acid ethyl ester.

11. The compound of claim 1 which is 4-amino-1-ethyl-1,2-dihydro-2-oxo-1,8-naphthyridine-3-carboxylic acid, n-butyl ester.

12. The compound of claim 1 which is 4-amino-1-ethyl-1,2-dihydro-2-oxo-1,8-naphthyridine-3-carboxylic acid hydrazide.

13. The compound of claim 1 which is 4-amino-1-ethyl-1,2-dihydro-2-oxo-1,8-naphthyridine-3-carboxylic acid or a pharmaceutically acceptable salt thereof.

14. The compound of claim 1 which is 4-diacetylamino-1-ethyl-1,2-dihydro-2-oxo-1,8-naphthyridine-3-carboxylic acid ethyl ester.

15. The compound of claim 1 which is 1-ethyl-1,2-dihydro-4-trifluoroacetylamino-2-oxo-1,8-naphthyridine-3-carboxylic acid ethyl ester.

16. The compound of claim 1 which is 1-ethyl-1,2-dihydro-4-(4-methyl-1-piperazinyl)-2-oxo-1,8-naphthyridine-3-carboxylic acid ethyl ester or a pharmaceutically acceptable salt thereof.

17. The compound of claim 1 which is 4-amino-1-propyl-1,2-dihydro-2-oxo-1,8-naphthyridine-3-carboxylic acid ethyl ester.

18. The compound of claim 1 which is 4-amino-1-isobutyl-1,2-dihydro-2-oxo-1,8-naphthyridine-3-carboxylic acid ethyl ester.

19. The compound of claim 1 which is 4-amino-1-cyclohexyl-1,2-dihydro-2-oxo-1,8-naphthyridine-3-carboxylic acid ethyl ester.

20. The compound of claim 1 which is 1-allyl-4-amino-1,2-dihydro-2-oxo-1,8-naphthyridine-3-carboxylic acid ethyl ester.

21. The compound of claim 1 which is 1-allyl-1,2-dihydro-7-methyl-2-oxo-4-(1-pyrrolidinyl)-1,8-naphthyridine-3-carboxylic acid ethyl ester.

22. The compound of claim 1 which is 1-allyl-4-chloroacetylamino-1,2-dihydro-2-oxo-1,8-naphthyridine-3-carboxylic acid.

23. The compound of claim 1 which is 1-propargyl-4-amino-2-oxo-1,8-naphthyridine-3-carboxylic acid ethyl ester.

24. The compound of claim 1 which is 4-amino-7-chloro-1-ethyl-1,2-dihydro-2-oxo-1,8-naphthyridine-3-carboxylic acid ethyl ester.

25. The compound of claim 1 which is 4-amino-7-ethoxy-1-ethyl-1,2-dihydro-2-oxo-1,8-naphthyridine-3-carboxylic acid ethyl ester.

26. The compound of claim 1 which is 4-amino-7-ethylamino-1,N-diethyl-1,2-dihydro-2-oxo-1,8-naphthyridine-3-carboxamide.

27. The compound of claim 1 which is 4-amino-1-ethyl-1,2-dihydro-7-methyl-2-oxo-1,8-naphthyridine-3-carboxylic acid ethyl ester.

28. The compound of claim 1 which is 4-amino-1-ethyl-1,2-dihydro-7-methyl-2-oxo-1,8-naphthyridine-3-carbonitrile.

29. The compound of claim 1 which is 4-amino-1-ethyl-1,2-dihydro-7-methyl-2-oxo-1,8-naphthyridine-3-carboxamide.

30. The compound of claim 1 which is 1-ethyl-1,2-dihydro-7-methyl-2-oxo-4-(1-pyrrolidinyl)-1,8-naphthyridine-3-carboxamide.

31. The compound of claim 1 which is 1-ethyl-1,2-dihydro-7-methyl-2-oxo-4-(1-pyrrolidinyl)-1,8-naphthyridine-3-carboxylic acid ethyl ester.

32. The compound of claim 1 which is 4-diethylamino-1-ethyl-1,2-dihydro-7-methyl-2-oxo-1,8-naphthyridine-3-carboxylic acid ethyl ester.

33. The compound of claim 1 which is 1-ethyl-1,2-dihydro-7-methyl-2-oxo-4-(4-methyl-1-piperazinyl)-1,8-naphthyridine-3-carboxylic acid or a pharmaceutically acceptable salt thereof.

34. The compound of claim 1 which is 1-ethyl-1,2-dihydro-7-methyl-4-(4-morpholinyl)-2-oxo-1,8-naphthyridine-3-carboxylic acid ethyl ester.

35. The compound of claim 1 which is 1-ethyl-1,2-dihydro-7-methyl-4-(4-methyl-1-piperazinyl)-2-oxo-1,8-naphthyridine-3-carboxylic acid ethyl ester or a pharmaceutically acceptable salt thereof.

36. The compound of claim 1 which is 1-ethyl-1,2-dihydro-7-methyl-2-oxo-4-(4-phenyl-1-piperazinyl)-1,8-naphthyridine-3-carboxylic acid ethyl ester or a pharmaceutically acceptable salt thereof.

37. The compound of claim 1 which is 1-ethyl-1,2-dihydro-4-[2-(hydroxyethyl)methylamino]-7-methyl-2-oxo-1,8-naphthyridine-3-carboxylic acid ethyl ester.

38. The compound of claim 1 which is 1-ethyl-1,2-dihydro-4-(3-dimethylaminopropylamino)-7-methyl-2-oxo-1,8-naphthyridine-3-carboxylic acid ethyl ester or a pharmaceutically acceptable salt thereof.

39. The compound of claim 1 which is 1-ethyl-1,2-dihydro-4-ethylamino-7-methyl-2-oxo-1,8-naphthyridine-3-carboxylic acid ethyl ester.

40. The compound of claim 1 which is 1-ethyl-1,2-dihydro-7-methyl-2-oxo-4-(1-piperazinyl)-1,8-naphthyridine-3-carboxylic acid ethyl ester or a pharmaceutically acceptable salt thereof.

41. The compound of claim 1 which is 4,4'-(1,4-piperazinediyl)-bis[1-ethyl-1,2-dihydro-7-methyl-2-oxo-1,8-naphthyridine-3-carboxylic acid]diethyl ester.

42. The compound of claim 1 which is 1-ethyl-1,2-dihydro-4-(4-carbethoxy-1-piperazinyl)-7-methyl-2-oxo-1,8-naphthyridine-3-carboxylic acid ethyl ester.

* * * * *